United States Patent
Gremel et al.

(10) Patent No.: US 6,524,267 B1
(45) Date of Patent: *Feb. 25, 2003

(54) VENOUS FILTER FOR ASSISTED VENOUS RETURN

(75) Inventors: Robert F. Gremel, Huntington Beach, CA (US); Roger J. Elgas, Anaheim Hills, CA (US)

(73) Assignee: Medtronic, Inc., Brooklyn Park, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/954,787

(22) Filed: Sep. 18, 2001

Related U.S. Application Data

(63) Continuation of application No. 09/251,619, filed on Feb. 17, 1999, now Pat. No. 6,302,860.

(51) Int. Cl.[7] .............................................. A61M 37/00
(52) U.S. Cl. ............... 604/6.09; 604/4.01; 604/5.01; 210/436; 422/44; 422/48
(58) Field of Search ............................ 604/4–6, 7, 65, 604/67, 73, 122, 405, 406, 4.01, 5.01, 6.09; 210/436, 739, 741, 744, 799, 805, 90; 422/44, 48, 45, 47

(56) References Cited

U.S. PATENT DOCUMENTS

| | | | | |
|---|---|---|---|---|
| 3,507,395 A | * | 4/1970 | Bentley | 210/443 |
| 4,411,783 A | | 10/1983 | Dickens et al. | 210/304 |
| 4,490,331 A | | 12/1984 | Steg, Jr. | 422/46 |
| 4,572,724 A | | 2/1986 | Rosenberg et al. | 55/159 |
| 4,676,771 A | | 6/1987 | Henke | 604/4 |
| 5,055,198 A | * | 10/1991 | Shettigar | 210/650 |
| 5,158,533 A | | 10/1992 | Strauss et al. | 604/4 |
| 5,162,102 A | * | 11/1992 | Nogawa et al. | 422/48 |
| 5,205,153 A | | 4/1993 | Hiavinka et al. | 73/79.03 |
| 5,270,005 A | | 12/1993 | Raible | 422/46 |
| 5,632,894 A | | 5/1997 | White et al. | 210/436 |
| 5,876,611 A | | 3/1999 | Shettigar | 210/739 |
| 6,302,860 B1 | * | 10/2001 | Gremel et al. | 604/6.09 |

* cited by examiner

Primary Examiner—Brian L. Casler
Assistant Examiner—Jennifer Maynard
(74) Attorney, Agent, or Firm—Stout, Uxa, Buyan & Mullins, LLP; Donald E. Stout; Daniel W. Latham

(57) ABSTRACT

The need for a venous reservoir in a heart-lung machine is obviated by using a vacuum-purged negative-pressure air filter in the venous return line ahead of the main blood pump. The purging vacuum for the venous air filter can also be used to purge air from the cardiotomy reservoir if a backflow-preventing valve is used on the venous air filter.

6 Claims, 2 Drawing Sheets

VENOUS FILTER FOR ASSISTED VENOUS RETURN

This application is a continuation under 35 U.S.C. 120 of application Ser. No. 09/251,619, Feb. 17, 1999 now U.S. Pat. No. 6,302,860, which patent is herein expressly incorporated by reference.

FIELD OF THE INVENTION

This invention relates to blood filters used in cardiopulmonary bypass circuits, and more particularly to a negative pressure blood filter for use in the venous line whether using assisted venous return techniques or not.

BACKGROUND OF THE INVENTION

Conventional cardiopulmonary bypass uses an extracorporeal blood circuit which includes a venous drainage line, venous reservoir, blood pump, oxygenator, and arterial filter. Blood circulation is accomplished by draining blood from the patient by gravity through the venous drainage line to the venous reservoir. From there, blood drains down to the blood pump, placing this portion of the circuit at a negative pressure with respect to atmosphere. The pump supplies positive pressure to return the blood to the patient through the oxygenator and filter. The venous reservoir holds blood volume as required, while both the venous reservoir and arterial filter remove air bubbles from the blood. These may cause health problems if returned to the patient in the arterial blood flow. Air can enter the circuit from a number of sources, including around the venous cannula and through various unanticipated intra-operative events. A further complication arises if a centrifugal pump is used, in which case a large volume of air will de-prime the pump, depriving it of its pumping capability.

In order to remove air from an extracorporeal circuit prior to its use, the circuit is primed with an appropriate solution. During surgery, this solution dilutes the patient's blood, and it is therefore desirable to minimize the volume required. The venous reservoir contains a relatively large volume of fluid, and recently it has been proposed to eliminate this component of the circuit. Several problems arise, however. Without the venous reservoir between the patient and the oxygenator, any air in the venous line will either accumulate in the centrifugal pump (if used) or be pumped into the oxygenator. Furthermore, if a large bolus of air is introduced, it may de-prime the pump and oxygenator. Although arterial filters are designed to capture air bubbles, they are not designed to handle larger volumes of air such as may occur from the causes described above. Also, arterial filters are located downstream of both the pump and the oxygenator, and therefore cannot prevent air problems that would occur in those devices. Furthermore, conventional arterial filters are designed to operate at positive blood pressures.

SUMMARY OF THE INVENTION

The present invention improves upon the design of an arterial filter to allow it to be used as a venous filter at a negative pressure and to capture larger volumes of air.

DESCRIPTION OF THE PREFERRED EMBODIMENTS

Figure 1:
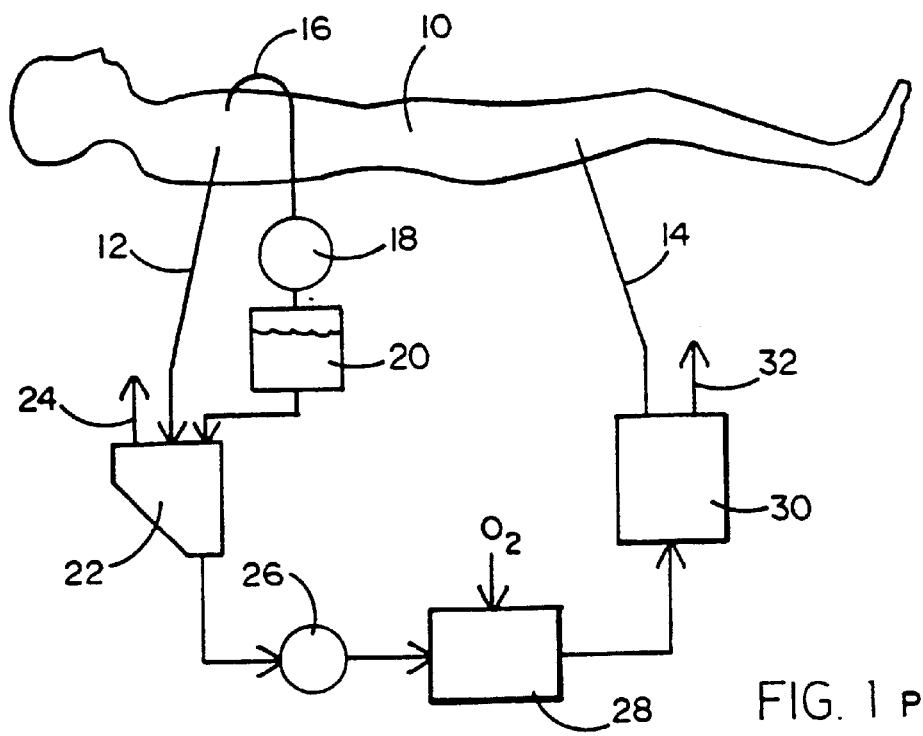
FIG. 1 is a schematic diagram of a conventional heart-lung machine.

Conventional heart-lung equipment, as schematically depicted in FIG. 1, draws the blood of a patient 10 during cardiovascular surgery through a venous line 12, oxygenates it, and returns the oxygenated blood to the patient 10 through an arterial line 14. Cardiotomy blood and surgical field debris are aspirated by a suction device 16 and are pumped by pump 18 into a cardiotomy filter 20.

In a conventional extracorporeal blood circuit, venous blood from line 12, as well as defoamed and filtered cardiotomy blood from filter 20, are discharged into a venous reservoir 22. In the reservoir 22, air entrapped in the venous blood (as, for example, air drawn into the blood circuit through the sutures, not shown, that attach the venous line 12 to a vein of the patient 10) rises to the surface of the blood in the reservoir 22 and is vented to atmosphere through a purge line 24. The purge line 24 is typically about a 6 mm ID line, and the air space above the blood in reservoir 22 is substantial.

In the conventional circuit of FIG. 1, a pump 26 draws blood from the reservoir 22 and pumps it through an oxygenator 28 and an arterial filter 30 into the arterial line 14. The arterial filter is basically a bubble trap that traps any microair bubbles larger than about 20–40 $\mu$m and discharges them to atmosphere through a typically about 1.5 mm ID purge line 32.

Figure 2:
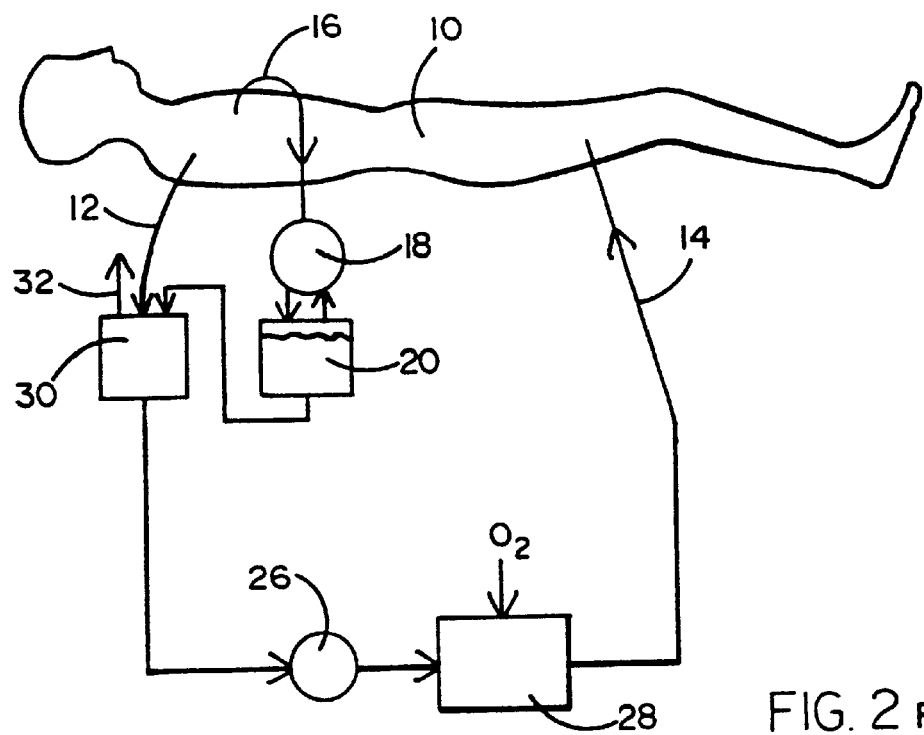
FIG. 2 is a schematic diagram of an AVR type heart-lung machine.

As shown in FIG. 2, it has recently been proposed to produce an assisted venous return (AVR) and to eliminate the reservoir 22, which accounts for a major portion of the priming volume of the extracorporeal blood circuit, by moving the arterial filter 30 into the venous line 12, upstream of the pump 26.

The filter 30 does not have an air space between its inlet and outlet, as the venous reservoir 22 does. Consequently, the negative pressure caused on the outlet side of filter 30 in FIG. 2 by the pump 26 is transmitted as suction to the venous line 12, thereby assisting the venous return from the patient 10.

Figure 3:
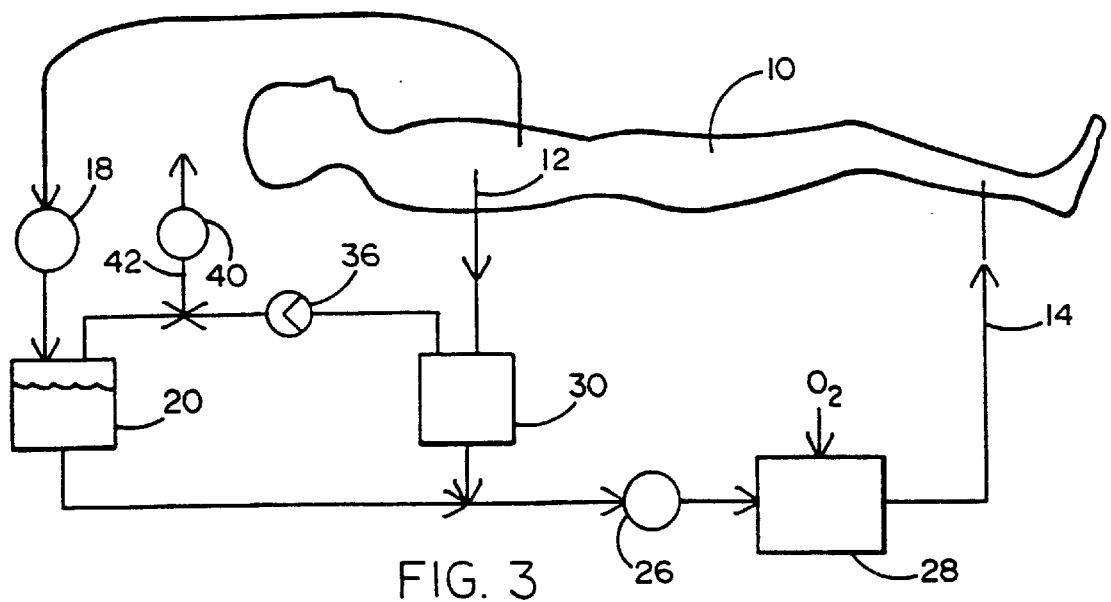
FIG. 3 is a schematic diagram of a heart-lung machine in accordance with the invention.

In accordance with the invention (FIGS. 3 and 4), a filter 30 of the type and size conventionally used as an arterial filter is adapted for efficient use as an AVR filter by several modifications. First, evacuation of air is facilitated by increasing the size of the purge port 34 to accept, e.g., a 6 mm ID purge line. Secondly, a vacuum greater than that normally used for venous drainage is applied to the purge port 34 to actively purge air from the filter 30. Thirdly, a check valve 36 is incorporated into the purge port to prevent air or blood from the cardiotomy reservoir 20 (which is at ambient pressure but is conveniently purged by the same vacuum that purges filter 30) from being drawn into the filter 30 by the negative pressure in filter 30, when the purging vacuum is not active. Fourthly, an air sensor 38 is provided in the filter 30 and is connected to activate the purge vacuum when, and only when, air is present in the filter 30. This prevents blood from being aspirated by the purging vacuum.

The purging vacuum may be produced by a pump 40, or it may be produced by connecting the purge line 42 to the vacuum outlet conventionally provided in operating rooms.

Figure 4:
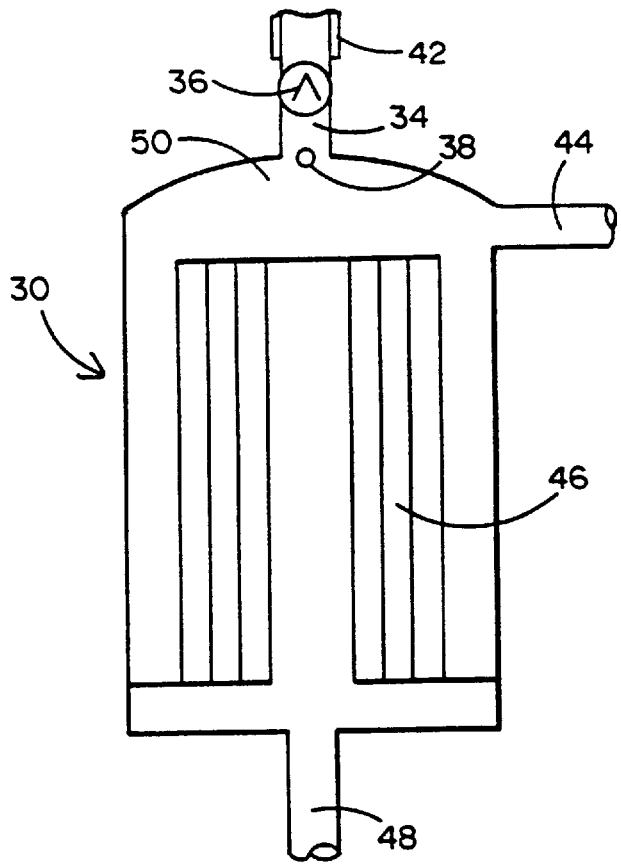
FIG. 4 is a partly schematic vertical section of the inventive filter.

FIG. 4 shows in somewhat schematic form the filter 30 of this invention. Blood enters the filter 30 through an inlet 44 and is drawn through the filter element 46 and into the outlet 48 by the action of pump 26. A screen (not shown) or other conventional bubble-trapping device traps any air bubbles in the blood stream and causes them to rise to the top 50 of filter 30. Normally, the filter 30 is filled with blood. When air begins to accumulate at the top of filter 30, this fact is sensed by the air sensor 38. The sensor 38 activates the vacuum in the purge line 22. The vacuum at the purge port 34 overcomes the negative pressure in the filter 30 and draws out any accumulated air, shutting off under the control of sensor 38 when all the air has been removed.

It is understood that the exemplary venous filter for assisted venous return described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

What is claimed is:

1. A method for extracorporeal oxygenation of a patient's blood during cardiopulmonary bypass surgery, the method comprising:
   receiving venous blood from a patient into a venous line;
   drawing venous blood through an air filter connected to the venous line with a first vacuum generated by a blood pump, the air filter comprising an air chamber;
   diverting air entering the air filter into the air chamber;
   sensing air in the air chamber;
   pulling a second vacuum, greater than the first vacuum, to draw air from the air chamber only when air is sensed in the air chamber;
   pumping blood exiting the air filter through the blood pump and through a blood oxygenator to oxygenate the blood; and
   returning the blood oxygenated by the blood oxygenator to an arterial system of the patient.

2. The method of claim 1, and further comprising drawing blood scavenged from a surgical site through a cardiotomy filter with a cardiotomy suction source, the step of pulling a second vacuum, greater than the first vacuum, to draw air from the air chamber only when air is sensed in the air filter comprising pulling the second vacuum with the cardiotomy suction source, the method further comprising preventing drawing of cardiotomy blood into the air filter using a check valve interposed between the air chamber and the cardiotomy suction source.

3. The method of claim 1, wherein venous blood is not collected in a venous reservoir.

4. The method of claim 1, wherein the step of pulling a second vacuum, greater than the first vacuum to draw air from the air chamber only when air is sensed in the air filter comprises pulling a second vacuum with a conventional vacuum outlet provided in an operating room.

5. The method of claim 1, wherein the step of pulling a second vacuum, greater that the first vacuum to draw air form the air chamber only when air is sensed in the air filter comprises pulling a second vacuum with a pump.

6. Apparatus for extracorporeal oxygenation of a patient's blood during cardiopulmonary bypass surgery, the apparatus comprising:
   venous line means for receiving venous blood from a patient;
   air filter means, connected to the venous line means, for separating air from blood, the air filter means comprising an air chamber and means for diverting air entering the air filter into the air chamber;
   blood oxygenating means for oxygenating blood after it is drawn through the air filter means;
   arterial line means for returning blood to the arterial system of the patient after the blood has been oxygenated by the blood oxygenating means;
   pump means, defining a first vacuum, for drawing blood through the venous line and air filter means and through the blood oxygenating means and arterial line means;
   sensing means for sensing air in the air chamber; and
   means for pulling a second vacuum, greater that the first vacuum, to draw air from the air chamber only when air is sensed in the air chamber by the sensing means.

* * * * *